United States Patent [19]
Mertelmeier et al.

[11] Patent Number: 6,157,697
[45] Date of Patent: Dec. 5, 2000

[54] APPARATUS USING X-RAYS AND MEASUREMENT OF ELECTRICAL POTENTIALS FOR EXAMINING LIVING TISSUE

[75] Inventors: Thomas Mertelmeier, Erlangen; Bernhard Scholz, Heroldsbach, both of Germany

[73] Assignee: Siemens Aktiengesellschaft, Munich, Germany

[21] Appl. No.: 09/274,730

[22] Filed: Mar. 23, 1999

[30] Foreign Application Priority Data

Mar. 24, 1998 [DE] Germany .......................... 198 12 974
Feb. 10, 1999 [DE] Germany .......................... 199 05 532

[51] Int. Cl.$^7$ ........................................... A61B 6/04
[52] U.S. Cl. .......................... 378/37; 600/547; 600/445; 600/430; 378/63
[58] Field of Search .................. 378/37, 95, 63; 600/445, 430

[56] References Cited

U.S. PATENT DOCUMENTS

| | | |
|---|---|---|
| 4,291,708 | 9/1981 | Frei et al. |
| 5,479,927 | 1/1996 | Shmulewitz ...................... 600/445 |
| 5,664,573 | 9/1997 | Shmulewitz . |
| 5,807,257 | 9/1998 | Bridges ...................... 600/430 |
| 5,810,742 | 9/1998 | Pearlman ...................... 600/547 |

OTHER PUBLICATIONS

"Breast cancer Screening by Impedance Measurements," Mertelmeier et al., *Frontiers Med. Biol. Engng.*, vol. 2, No. 2, pp. 111–117.

"Second–Generation Compilers Optimize Semicustom Circuits," Mertelmeier et al., *Electronic Design*, Feb. 19, 1987, No. 4, pp. 92–96.

"A Review of Image Reconstruction Techniques for Electrical Impedance Tomography," *Med. Phys.*, vol. 16, No. 2, Mar./Apr. 1989, pp. 162–169.

*Primary Examiner*—David P. Porta
*Assistant Examiner*—Pamela R. Hobden
*Attorney, Agent, or Firm*—Schiff Hardin & Waite

[57] ABSTRACT

In an apparatus for examining living tissue by means of X-rays and by electric impedance measurement, a control device optionally activates an X-ray source and a radiation receiver, and/or for applying current or voltage signals to the tissue to be examined and a unit for measuring induced potentials or currents. This allows an X-ray image to be produced and induced potentials and currents to be measured either simultaneously or sequentially. It is also possible to fuse the respective images produced in these ways.

12 Claims, 3 Drawing Sheets

APPARATUS USING X-RAYS AND MEASUREMENT OF ELECTRICAL POTENTIALS FOR EXAMINING LIVING TISSUE

BACKGROUND OF THE INVENTION

1. Field of the Invention

The present invention relates to an apparatus for examining living tissue of the type used, for example, to examine a female breast for tumors.

2. Description of the Prior Art

An apparatus known from U.S. Pat. No. 4,291,708, has an electrode arrangement which interacts electrically with the tissue to be examined. Also provided are means for applying current signals to the electrode arrangement and means for measuring potentials induced by the current signals in the tissue to be examined, which likewise cooperate with the electrode arrangement. The dielectric constants are determined for different regions of the breast from the measured values thus determined in order to be able to reach a conclusion as to the presence or absence of a tumor from the changes in the dielectric constants.

It is an advantage of this apparatus that it can operate without ionizing radiation and non-invasively. Experience with such apparatuses has shown, however, that sensitivity and specificity leave something to be desired in comparison with classic X-ray mammography.

Known mammography X-ray systems have an X-ray source, a radiation receiving arrangement disposed opposite the X-ray source, for X-rays emanating from the X-ray source, and a compression device, arranged between the X-ray source and the radiation receiver, for the tissue to be examined.

SUMMARY OF THE INVENTION

It is an object of the present invention to provide an apparatus of the type initially described wherein it is possible to examine the individual to be examined in a way which produces as little risk or discomfort as is possible, and at the same time is as reliable as possible.

The above object is achieved in accordance with the principles of the present invention in an examination apparatus having an X-ray source and an X-ray receiver for producing an X-ray image, and an electrical impedance measurement arrangement for producing electrical impedance data, and a control unit which allows an X-ray image to be obtained, and electrical impedance data to be generated, either in sequence or substantially simultaneously.

Thus, it is possible by means of the invention to use a single apparatus to examine living tissue optionally only by means of X-rays or only by means of electric impedance measurement, or by a combination of X-rays and electric impedance measurement. In the latter case the examinations optionally can be carried out sequentially or substantially simultaneously.

It is thereby possible to select an examination procedure which is well adapted to the respective examination subject with regard to the stress on the individual to be examined, and to reliability. In this connection, it is particularly advantageous that in cases in which examination is performed by means of both X-rays and electric impedance measurement, the tissue to be examined can remain in the same position in the compression device, with the result that the two examination results can be optimally compared. This is clearly not the case when it is necessary to work two separate apparatuses, since it is virtually impossible to compress the tissue to be examined in the same way in both apparatuses.

The impedance measurement can be carried out by applying current signals and measuring induced potentials, or alternatively by applying voltage signals and measuring the induced currents.

In order to prevent the individual electrodes required for impedance measurement from disadvantageously influencing the X-ray images, in accordance with one embodiment of the invention the individual electrodes are formed of a material which attenuates X-rays poorly. In order entirely to avoid disadvantageous influences of the electrode arrangement on the X-ray images, in a preferred embodiment of the invention the electrode arrangement has an electrically inactive region which is formed so that during imaging it uses the X-rays emanating from the X-ray source to produce on the radiation receiver an image which is the inverse of the image of the individual electrodes and has the same optical density as the image of the individual electrodes. It is true that in this case there is a certain attenuation of the X-rays by the electrode arrangement, but the presence of the electrode arrangement in the X-ray images is virtually undetectable.

In a preferred embodiment of the invention a central processor calculates a preferably three-dimensional distribution of impedance values on the basis of digital data corresponding to the potentials measured by a unit for measuring induced potentials, or currents measured by a unit for measuring induced currents. The central processor calculates the distribution of impedance values, preferably by using an image reconstruction technique. Suitable reconstruction techniques are described, for example, in "A review of image reconstruction techniques for electrical impedance tomography", D. C. Barber, Med. Phys., Vol. 16, No. 2, March/April 1989, Am. Assoc. Phys. Med., pages 162–169.

In a further preferred embodiment of the invention, by taking account of the coordinate systems which are the basis for producing the X-ray image and determining the three-dimensional distribution of the impedance values, the central processor fuses at least a portion of the three-dimensional distribution of the impedance values with digital data corresponding to the X-ray image to form a fusion image. In this case, the fusion image is advantageously produced in such a way that the central processor projects the three-dimensional distribution of the impedance values into the X-ray image. It is also possible to project only one or more layers of the three-dimensional distribution of the impedance values into the X-ray image.

In a further version of the invention, it is also possible for the central processor to produce the fusion image by inserting the X-ray image into one of the layers of the three-dimensional distribution of the impedance values.

The radiation receiver is preferably a radiation receiver which generates an X-ray image with appropriate digital data which are fed to a central processor. It is also possible to employ a radiation receiver which generates the X-ray image with appropriate analog signals, in which case a converter is provided for converting the analog signals into digital data which correspond to the X-ray image and which are fed to a central processor. Another alternative is to employ a radiation receiver formed by a film for X-ray images, and a digitizer which scans the exposed film and supplies digital data which correspond to the X-ray image and which are fed to a central processor.

DESCRIPTION OF THE PREFERRED EMBODIMENTS

Figure 1:
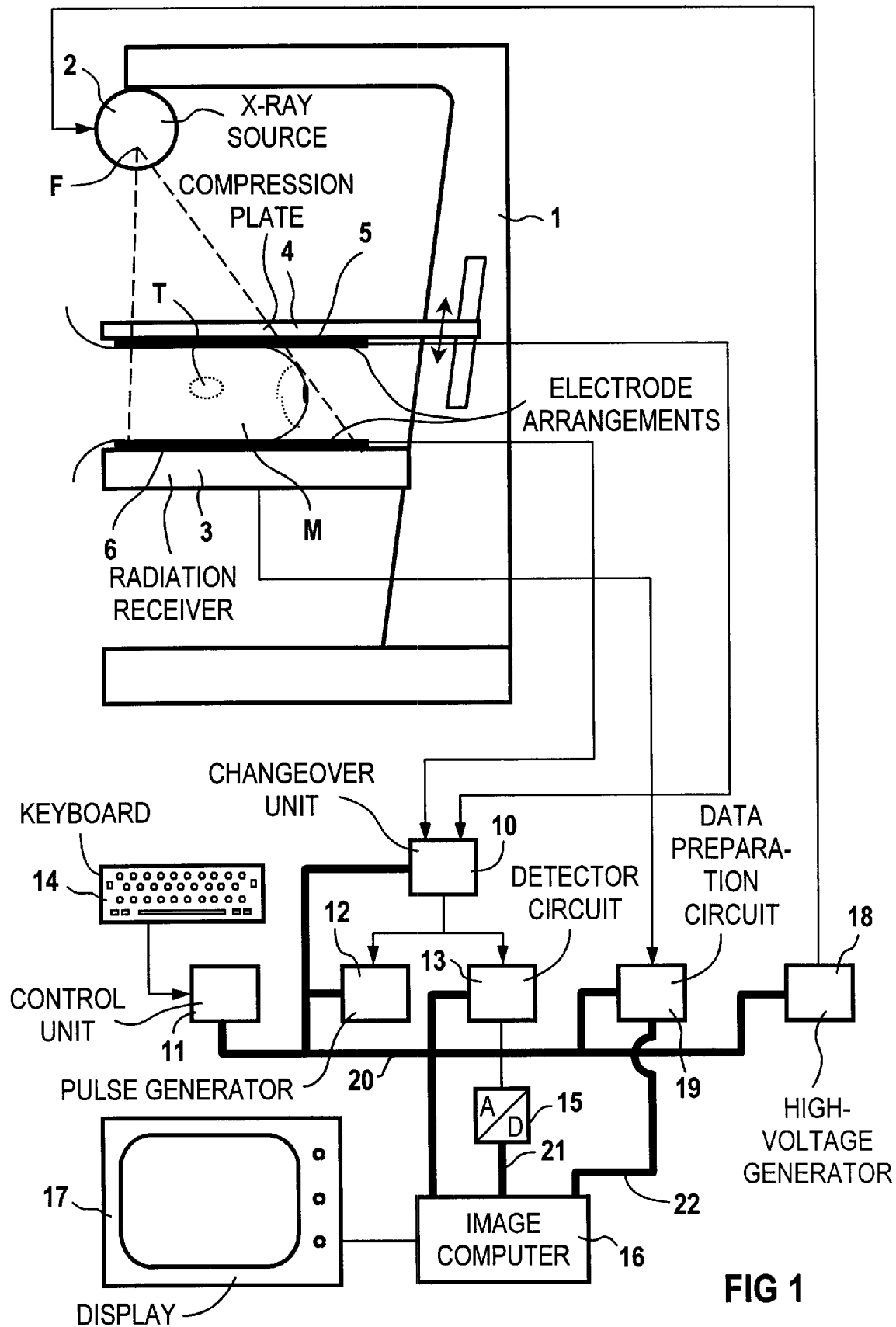
FIG. 1 shows an apparatus according to the invention, partly in the form a block diagram.

The apparatus represented in FIG. 1 serves the purpose of detecting tumors in living tissue, and has a stand 1 on which an X-ray source 2 and a radiation receiver 3 are fitted opposite one another so that the X-ray beam, which emanates from the focus F of the X-ray source 2 and is indicated by dashes, strikes the radiation receiver 3.

The radiation receiver 3 is of a type which produces an output of digital signals corresponding to the received X-ray image, i.e., a flat image converter based on amorphous silicon (a:Si), for example.

A compression plate 4 formed, for example, from material which is effectively transparent to X-rays, is arranged on the stand 1 between the X-ray source 2 and the radiation receiver 3 in an adjustable fashion such that tissue to be examined, for example—as represented in FIG. 1 —a female breast M containing a tumor T, can be compressed between the radiation receiver 3 and the compression plate 4. The compression plate 4 and the radiation receiver 3 thus form a compression device.

Figure 2:
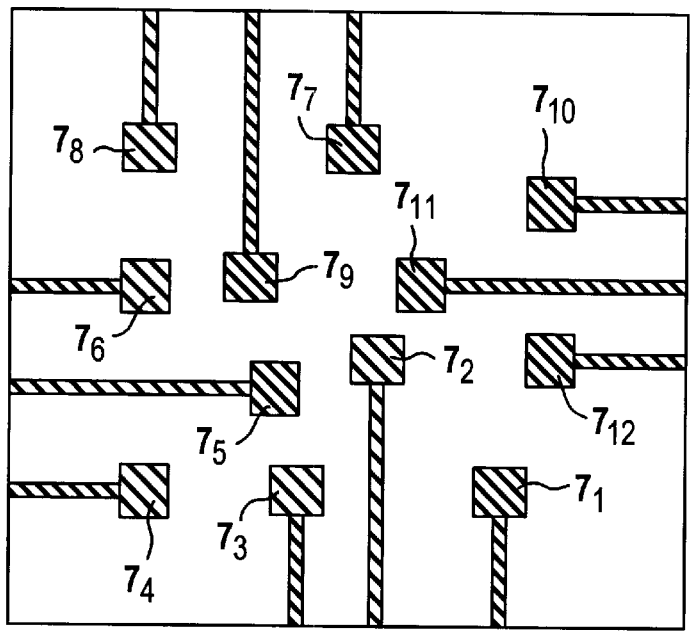
FIG. 2 shows a view of a first layer of the electrode arrangement of the apparatus in accordance with FIG. 1.
Figure 3:
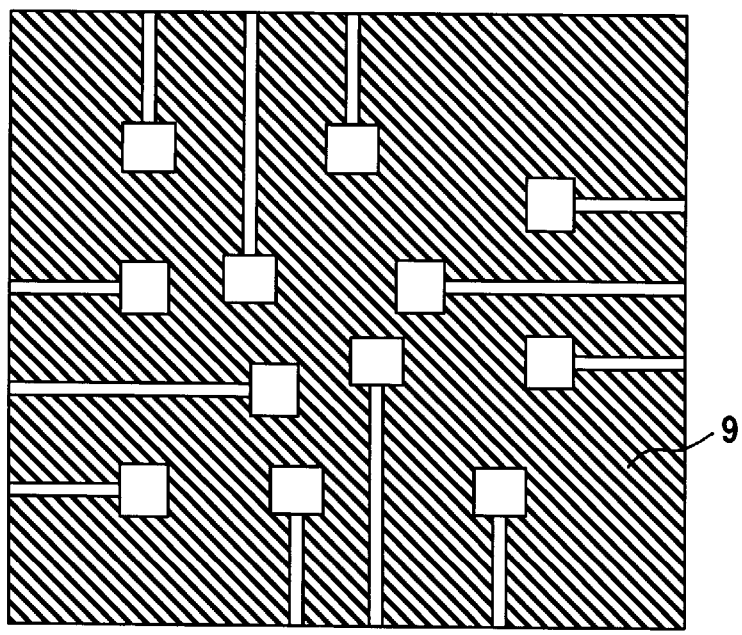
FIG. 3 shows a view of a second layer of the electrode arrangement of the apparatus in accordance with FIG. 1.
Figure 4:
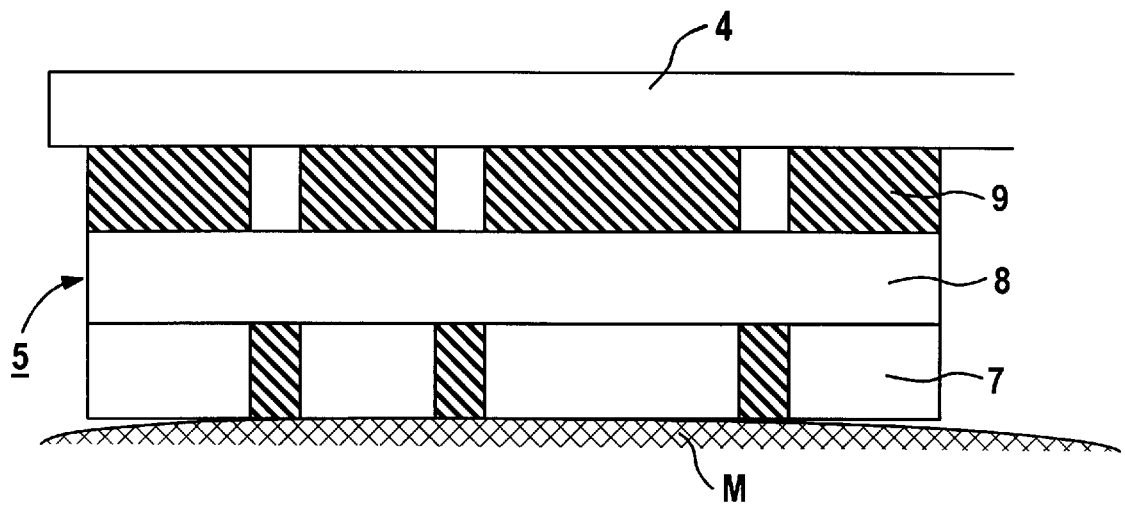
FIG. 4 shows a part of the compression device of the apparatus in accordance with FIG. 1, in cross section.

Provided on the mutually opposite surfaces of the radiation receiver 3 and the compression plate 4 are electrode arrangements 5, 6 which are illustrated in more detail in FIGS. 2 to 4, and which interact electrically with the tissue compressed between the radiation receiver 3 and the compression plate 4. This electric interaction can be ensured, for example, by a gel.

As can be seen from FIG. 4, using the example of the electrode arrangement 5 (the electrode arrangement 6 being of corresponding design), the electrode arrangement 5 is formed of three layers and is fixed to the compression plate 4. In the lowermost layer 7 in FIG. 2, there are electrically active individual electrodes which are used (as described in more detail below) for the purpose of electric impedance measurement. An example of such an arrangement of the individual electrodes $7_1$ to $7_{12}$ is illustrated in FIG. 3.

Subsequently, an insulating layer 8 is provided which separates the individual electrodes $7_1$ to $7_{12}$ from an electrically inactive region 9 which forms the third layer of the electrode arrangement 5 and which is formed as shown in FIG. 3 so that it is inverse with respect to the arrangement of the individual electrodes $7_1$ to $7_{12}$;

Just like the electrically inactive region 9 of the electrode arrangement 5, the individual electrodes $7_1$ to $7_{12}$ are formed, for example, of film-like conductor material made of carbon. The insulating layer 8 is also film-like material, for example cellophane. Thus, the electrode arrangement 5 can be considered as a film-like printed circuit which is connected to the compression plate 4, for example by bonding. Suitable electrodes are available, for example, from Joiko, Germany and Medicotest, Denmark.

Since the individual electrodes $7_1$ to $7_{12}$ and the electrically inactive region of the electrode arrangement 5 not only are formed from the same material, but also have the same thickness, imaging the electrically inactive region by means of the X-rays emanating from the X-ray source 2 produces an image which is the inverse of the image of the individual electrodes $7_1$ to $7_{12}$ and has the same optical density as the image of the individual electrodes $7_1$ to $7_{12}$. Since the electrode arrangement 5 employs thin films, and is thus very thin overall, the fact that the X-ray projection is a perspective projection does not affect the invisibility of the electrode arrangement 5 in the image.

Thus, the electrode arrangement 5 (and the same holds for the correspondingly designed electrode arrangement 6) is invisible in an X-ray image produced by means of the X-ray source 2 and the radiation receiver 3.

As is shown diagrammatically in FIG. 1, the electrode arrangements 5 and 6, specifically their individual electrodes, can optionally be connected via a changeover unit 10, which can be actuated by a control unit 11, to a unit for applying electric signals to at least some of the individual electrodes, specifically a pulse generator 12, or a unit for measuring electric signals induced by these electric signals in the tissue to be examined, specifically a detector circuit 13. This arrangement is represented as a single-channel circuit in FIG. 1 for clarity, but in practice the arrangement must be of multichannel design, it being possible for the number of channels to correspond at most to the number of individual electrodes.

A keyboard 14 connected to the control unit 11 can be used to select an operating mode in which the pulse generator 12 emits current signals and the detector unit 13 measures the potentials induced as a consequence of the current signals. Alternatively, the keyboard 14 can be used to select another operating mode, in which the pulse generator 12 emits voltage signals and the detector unit 13 measures the currents induced as a consequence of the voltage signals.

The electrode arrangements 5, 6, the control unit 11, the changeover unit 10, the pulse generator 12 and the detector unit 13 cooperate, for the purpose of conducting an examination, via a control bus 20 in such a way that, in successive fashion, the changeover unit 10 is used to connect different combinations of individual electrodes to the pulse generator 12, which applies pulse-like electric signals to the connected electrodes, while other individual electrodes are connected via the changeover unit 10 to the detector unit 13, resulting in signals being available at the output of the detector unit 13 which correspond to the electric signals induced in the tissue to be examined as a consequence of the pulse-like electric signals. The pulse-like electric signals can be mono-frequency or multi-frequency signals in a known way.

The pattern in accordance with which the pulse-like electric signals are applied to successive individual electrodes can be entered by the keyboard 14, or can be selected from a number of patterns stored in the control unit 11.

The output signals of the detector unit 13 pass via an analog/digital converter 15 and a dataline 21 to an electronic central processor, specifically the image computer 16, which uses the digital data corresponding to the output signals of the detector unit 13 in accordance with the algorithm of a known reconstruction technique to calculate and store a three-dimensional distribution of impedance values, for example the dielectric constant, the conductivity and the like.

This three-dimensional distribution of the impedance values, or preferably several flat layers (slices) of the three-dimensional distribution of the impedance values, can be represented on a display device 17 connected to the image computer 16 once the impedance values have been converted by the image computer 16 into corresponding grey-scale values or tri-stimulus values.

The X-ray source 2 is supplied by a high-voltage generator 18 connected thereto. The radiation receiver 3 and the control unit 11 cooperate via a control bus 20 in such a way that the high-voltage generator 18 activates the X-ray source 2 with values for the operating parameters of X-ray voltage, X-ray current and mAs product, which can be selected via the keyboard 14 or can correspond to one of several operating parameter sets, which can be selected by the keyboard 14 and are stored in the control unit 11. The digital data which are then available at the output of the radiation receiver 3 and correspond to the X-ray image exposure, then pass via a data preparation circuit 19 and a dataline 22 to the image computer 16 which stores the digital data corresponding to the X-ray image and, if appropriate after carrying out image postprocessing, can represent the data on the display device 17 as grey-scale values or tri-stimulus values.

The keyboard 14 can be used to select different operating modes of the apparatus, specifically a first operating mode in which only electric impedance measurement takes place, a second operating mode in which only an X-ray examination is performed and a third operating mode in which an X-ray examination and an electric impedance measurement are carried out simultaneously.

It is thereby possible to produce and carry out examination cycles which are well adapted to the respective case of examination.

Since both the three-dimensional distribution of the impedance values and the digital data corresponding to the X-ray image are stored in the image computer 16, the image computer is capable, by taking account of the coordinate systems which are the basis for producing the X-ray image and determining the three-dimensional distribution of the impedance values, of fusing at least a portion of the three-dimensional distribution of the impedance values with digital data corresponding to the X-ray image to form a fusion image.

Figure 5:
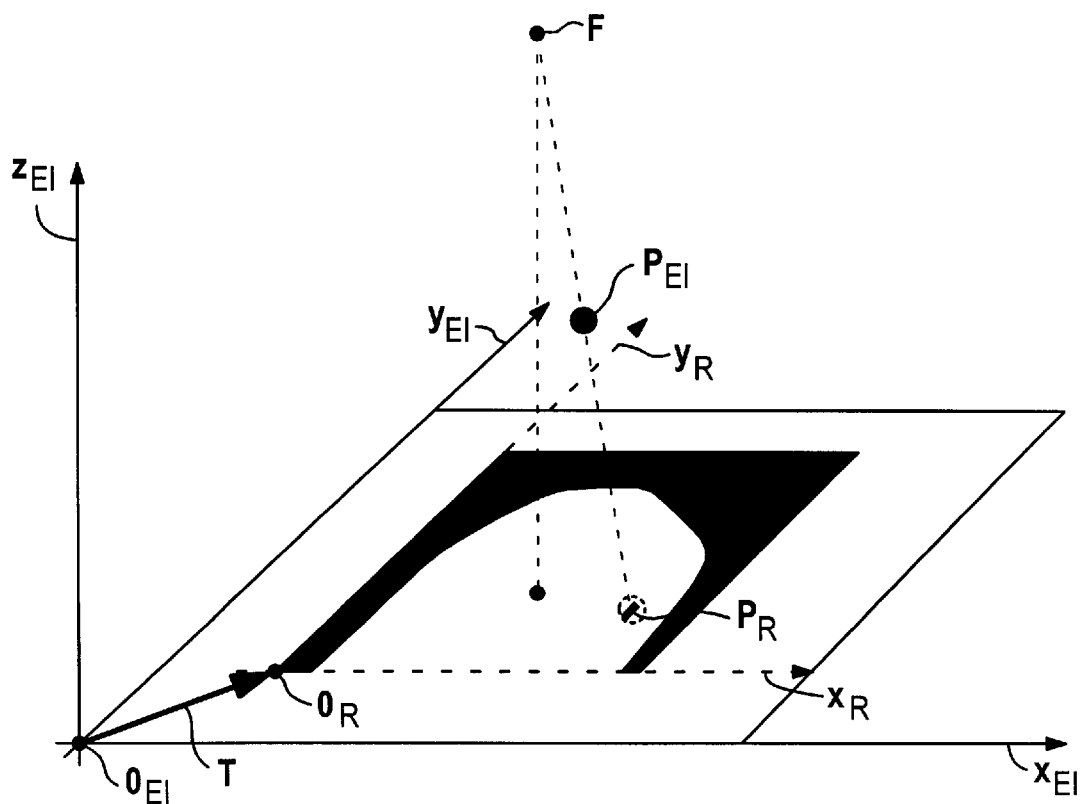
FIG. 5 shows a diagram illustrating the image processing in the case of the apparatus in accordance with FIG. 1.

As can be seen from FIG. 5, the individual values of the three-dimensional distribution of the impedance values relate to a spatial rectangular coordinate system with axes $x_{EI}$, $y_{EI}$ and $z_{EI}$ and the origin $O_{EI}$. The digital data corresponding to the X-ray image constitutes a planar distribution of pixels in a rectangular plane coordinate system with axes $y_R$ and $x_R$, and an origin $O_R$. The axes $y_R$ and $x_R$ proceed parallel to the axes $y_{EI}$ and $x_{EI}$ and lie in the same plane as $y_{EI}$ and $x_{EI}$. The two coordinate systems are thus connected via a translation vector T.

In order to produce a fusion image, the image computer 16 projects values of the three-dimensional distribution of the impedance values in accordance with the laws of central projection, starting from a projection center Z, whose position relative to the $x_R$–$y_R$ plane corresponds to the position of the focus F of the X-ray source 2 relative to the radiation receiver 3, into the X-ray image. This is illustrated in FIG. 5 for a value $P_{EI}$ the three-dimensional distribution of the impedance values, which is then imaged in the X-ray image at the point $P_R$.

Thus, an effect is achieved which corresponds, so to speak, to imaging the three-dimensional distribution of the impedance values on the radiation receiver 3 by means of the X-ray source 2.

In this case, depending on appropriate inputs, the keyboard 14 can be used to project the three-dimensional distribution of the impedance values in its entirety, or only three-dimensional subsets of the three-dimensional distribution of the impedance values into the X-ray image. Furthermore, it is possible for two-dimensional subsets of the three-dimensional distribution of the impedance values, preferably layers of the three-dimensional impedance values proceeding parallel to the plane of the X-ray image, to project into the X-ray image, it being possible to use the keyboard 14 to select the coordinate $z_{EI}$ of the layer to be projected.

Alternatively, the image computer 16 can produce a fusion image by inserting the X-ray image into a plane, which can be prescribed by the user via the keyboard 14, of the three-dimensional distribution of the impedance values, whose coordinate $z_{EI}$ can be selected by means of the keyboard 14. In this case, the image computer 16 recalculates in advance the digital data corresponding to the X-ray image, doing so in such a way that the data obtained correspond to the representation of the X-ray image in the plane corresponding to the selected layer.

Regardless of the way in which a fusion image is produced, by comparison with conventional X-ray images or conventional images obtained on the basis of electric impedance measurements, it offers extended diagnostic possibilities enabling an immediate detection of whether peculiarities in the X-ray image correspond to the peculiarities in the three-dimensional distribution of the impedance values.

The fusion images obtained in this case with the aid of the apparatus according to the invention are therefore particularly revealing because of the fact that during the X-ray examination and during the electric impedance measurement, the region of the tissue to be examined remains in the same position in the compression device. This holds to a particularly great extent when the X-ray examination and the electric impedance measurement are carried out simultaneously.

Otherwise, it is possible to provide in addition to the compression plate 4 and the radiation receiver 3, further lateral compression plates provided with electrode arrangements, with the result that the reconstruction of the three-dimensional distribution of the impedance values is possible not only on two sides with reference to a ventral-dorsal axis (mamilla-rib point of impingement) but also on all sides.

The exemplary embodiment of the apparatus according to the invention has been described above in the context of examination of a female breast. Any other regions of tissue of any desired individuals, however, can be examined using the apparatus according to the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for examining living tissue comprising:

an X-ray source which emits X-rays;

a compression device disposed in a path of said X-rays for compressing tissue;

a radiation receiver disposed in said path of said X-rays and producing data representing an X-ray image of said tissue;

an electrode arrangement disposed on said compression device having a plurality of electrodes which interact electrically with tissue compressed in said compression device;

a signal source for applying signals from the group of signals consisting of current signals and/or voltage signals to at least some of said electrodes in said plurality of electrodes;

a measurement device for measuring induced signals selected from the group consisting of induced potentials and/or induced currents which are induced in said tissue compressed in said compression device by said signals from said signal source; and a control unit connected to said X-ray source and to said signal source for optionally activating said X-ray source and said signal source in a sequence or substantially simultaneously.

2. An apparatus as claimed in claim 1 wherein said plurality of electrodes are comprised of a material which is substantially transparent to said X-rays.

3. An apparatus as claimed in claim 1 wherein said electrode arrangement comprises an electrically inactive region in said path of said X-rays for producing on said radiation receiver an image which is an inverse of an image of said plurality of electrodes and having substantially a same optical density as said image of said plurality of electrodes.

4. An apparatus as claimed in claim 1 wherein said compression device has a region disposed in said path of said X-rays, said region being comprised of material which is substantially transparent to said X-rays.

5. An apparatus as claimed in claim 1 wherein said induced signals comprise analog signals, and further comprising a converter for converting said analog signals into digital signals, and a processor supplied with said digital signals for calculating a distribution of impedance values in said tissue from said digital signals.

6. An apparatus as claimed in claim 5 wherein said central processor calculates said distribution of impedance values using a reconstruction algorithm.

7. An apparatus as claimed in claim 5 wherein said processor calculates a three-dimensional distribution of said impedance values.

8. An apparatus as claimed in claim 7 wherein said X-ray image has an X-ray image coordinate system associated therewith and wherein said distribution of impedance values has a distribution coordinate system associated therewith, and wherein said data representing said X-ray image are supplied to said processor, and wherein said processor fuses at least a portion of said three-dimensional distribution of impedance values with said data representing said X-ray image to form a fusion image.

9. An apparatus as claimed in claim 8 wherein said processor produces said fusion image by projecting said three-dimensional distribution of impedance values onto said X-ray image.

10. An apparatus as claimed in claim 8 wherein said three-dimensional distribution of impedance values comprises a plurality of layers, and wherein said processor produces said fusion image by projecting at least one of said layers onto said X-ray image.

11. An apparatus as claimed in claim 8 wherein said three-dimensional distribution of impedance values comprises a plurality of layers, and wherein said processor produces said fusion image by inserting said X-ray image into one of said layers.

12. An apparatus as claimed in claim 1 wherein said data representing said X-ray image comprise digital data.

\* \* \* \* \*